United States Patent

Fröjd

[11] Patent Number: 5,744,806
[45] Date of Patent: Apr. 28, 1998

[54] METHOD FOR MULTISENSOR ARRANGEMENTS

[75] Inventor: Christer Fröjd, Sundsvall, Sweden

[73] Assignee: AFP Imaging Corporation, Elmsford, N.Y.

[21] Appl. No.: 793,277

[22] PCT Filed: Sep. 8, 1995

[86] PCT No.: PCT/SE95/01011

§ 371 Date: Mar. 5, 1997

§ 102(e) Date: Mar. 5, 1997

[87] PCT Pub. No.: WO94/07354

PCT Pub. Date: Mar. 14, 1996

[30] Foreign Application Priority Data

Sep. 8, 1994 [SE] Sweden ................... 9402997

[51] Int. Cl.⁶ .................. H05G 1/64; H01L 25/00
[52] U.S. Cl. .................. 250/370.09; 378/19; 378/40
[58] Field of Search .......... 250/370.09; 378/38, 378/40, 39, 19

[56] References Cited

U.S. PATENT DOCUMENTS

| | | | |
|---|---|---|---|
| 4,070,578 | 1/1978 | Timothy et al. | 250/370.09 |
| 4,823,369 | 4/1989 | Guenther et al. | 378/22 |
| 4,878,234 | 10/1989 | Pfeiffer et al. | 378/40 |
| 5,018,177 | 5/1991 | McDavid et al. | 378/62 |

FOREIGN PATENT DOCUMENTS 0204676  12/1986  European Pat. Off.
0215757  3/1987   European Pat. Off.

OTHER PUBLICATIONS

Chapter 2, "Theory of Rotational Panoramic Radiography", second edition of Panoramic radiology, Olaf Langland, Robert Langlais, Doss McDavid and Angelo DelBalso, Printed by Lea & Febiger, Philadelphia 1989, pp. 38–75.

Primary Examiner—Don Wong
Attorney, Agent, or Firm—Young & Thompson

[57] ABSTRACT

The present invention is providing a method and a sensor device arrangement for a scanning digital radiographic system offering a multiple sensor arrangement producing continuous image data acquisition along the entire length of the detector device arrangement. By cutting the sensor die short edges along a die cut (46) with a predefined angle in relation to the scanning direction there is no longer a total loss of data at any position along the longitudinal extension of the detector arrangement. Instead some minor loss pixels (40) is encountered over a certain range of the scanning width coinciding with the joint of two adjacent sensor dies, in which range the image can easily be fully reconstructed by means of the electronic circuitry.

12 Claims, 5 Drawing Sheets

5,744,806

1

METHOD FOR MULTISENSOR ARRANGEMENTS

TECHNICAL FIELD

The present invention relates to sensors for x-ray imaging and more particularly to a multi sensor arrangement for a scanning digital radiographic system.

PRIOR ART

Since the middle of 1950 a common method to produce overview x-ray images of teeth and jaws for use in dentistry is the so called panoramic x-ray method. FIG. 1. demonstrates a typical prior art set up. Assuming the head of the patient is oriented in an upright position, the method uses a movable x-ray source 1 with the, beam collimated to a narrow (3–6 mm) width in the horizontal dimension, and elongated at least 12 cm in the vertical dimension. The collimation is done with a narrow slit in a piece of sheet metal made of an x-ray absorbing material placed at a suitable distance from the focal spot of the x-ray tube, but before the radiation reaches the patient. On the opposing side of the patient, relative to the x-ray source, a second metal plate 3 with a narrow second slit, corresponding to the fan shaped beam is placed. The slits and the x-ray source with it's collimator are rigidly attached to each other. A film 5 is placed further away from the x-ray source, in the direction of the x-ray beam, at a position behind the second slit. During the exposure, usually taking 15–20 seconds for an ordinary panoramic x-ray, 30 cm wide, the arrangement of x-ray source and slit is rotated in a direction 3 around the head of the patient in a controlled manner so that a rotational center 7 of the imaging system will be situated within the head of the patient. At the same time, the imaging system will move relative to the film which will be exposed by radiation through the patients head and the second slit, piece by piece, until all of the film has been exposed during the time the imaging system was rotated around its rotational center 7.

By controlling the film speed relative to the object, the x-ray beam and the projection geometry with the rotational center assumed as a "virtual focus" that is moved during the exposure, it can be demonstrated that only a predetermined layer in the object is sharply depicted. In order to bring this sharp layer to coincide with the dental arches and to compensate for magnification variations in the vertical and horizontal dimensions, a rather complex motion sequence is required, where the vertically oriented rotational axis 7 is not fixed within the patients head but will be moving along a continuous path in the horizontal plane approximately parallel to the occlusal plane according to FIG. 2.

A good reference for a popular technical description of conventional panoramic radiography is found in chapter 2, "Theory of Rotational Panoramic Radiography", second edition of "Panoramic radiology" by Olaf Langland, Robert Langlais, Doss McDavid, Angelo DelBalso, printed by Lea & Febiger, Philadelphia 1989.

The traditional method can be viewed, as indicated in FIGS. 3 and 4, as a method to add an indefinite number of images, each of them with indefinitely low exposure, in size corresponding to the slit, directly on to the analog film medium, simultaneously moving the film past the slit as described above. However, the method would work equally well using a large but finite number of discrete steps both in the x-ray source/slit assembly motion and in the motion of the film.

2

It is obvious that the described method could be modified to utilize for instance semiconductor detectors replacing the film. Three examples of relevant patents are the U. S. Pat. Nos. 4,878,234, 4,823,369 and 5,018,177.

The first patent document U.S. Pat. No. 4,878,234 deals with a method and an apparatus to use one or several CCD (Charge Coupled Device) detectors for both detecting the image information and for simulation of the film motion directly in the imaging area by, since the early development of CCD:s, the well known method named TDI (Time Delayed Integration) wherein the individual pixel charges can be moved to simulate film motion by the clocking sequence of the detector. This method has the same limitations as the film method regarding the necessary complex motion pattern to adjust the horizontal magnification and to determine the position of the sharp layer. An obvious drawback is that the position of this layer has to be predetermined, before the exposure. The image is digitized during the exposure sequence and immediately subsequently presented on a video monitor.

The second patent publication U.S. Pat. No. 4,823,369 deals with a method and an apparatus to capture a large number of overlapping images using a semiconductor image detector with a dimension corresponding to the above described slit, in real time postprocessing each of the images by adding pixels adjacent to each other to create fewer columns of image data to reduce the amount of data. Each of the resulting conbined columns would correspond to a readout register of a detector as described in the previous U.S. Pat. No. 4,878,234 or to an ordinary image column with reduced spatial resolution. Image data from the set of columns after postprocessing is stored at separate locations in a large image memory. A reconstruction of panoramic images is performed after the completion of the exposure by adding the images stored in memory to another memory, slightly positionally shifted relative to each other, until one or more resulting images with a size corresponding to approximately 12.5×30 cm has been totally covered using the sums of a large number of smaller images.

This method reduces the spatial resolution or restricts the subsequent reconstruction to a restricted number of predetermined layers depending on how many groups of image column data that will be created during the data reduction.

It should be noted that in both above disclosed patent documents a secondary diaphragm is included as a necessary requirement in all the independent claims. However, a secondary diaphragm would be completely unnecessary when a large area film is replaced by a detector which only picks up radiation falling within the borders of the sensitive area.

The third document U.S. Pat. No. 5,018,177 discloses a method and an apparatus for producing among other possible projections, panoramic radiograms, using one single, vertically oriented line detector, consisting of a number of pixel detectors. This document mainly deals with the idea to divide the complete predetermined scanning period into a series of time intervals which are a function of the elapsed time within the total scanning period. The signal created by radiation in the detector is integrated during each time interval. At the end of each time interval the analog signal from the detector is converted to digital data. By means of data processing a complete two dimensional radiogram is produced from the set of column data from the detector. The disclosure also deals with a way to calculate the described time intervals from a given projection geometry and a given predetermined scanning time interval to obtain a panoramic radiogram.

Thus a common method for imaging large objects is to scan over the object using a linear sensor, for example a diode array, or a narrow two-dimensional sensor, for example a CCD or any other two dimensional pixel array. Since the length of the sensor is limited by the wafer size and the processing capabilities to about 5–8 cm the scan width using a single sensor is also limited.

The solution for wider objects is to either scan in two dimensions or to increase the scan width by mounting a number of sensors in line. Two-dimensional scanning complicates the mechanics and also tends to take too much time for many applications.

The general available sensors today are rectangular or square formed. When mounting multiple rectangular or square sensors in line data will be always lost in the border region between the individual sensors. The active area can not be extended all the way to the edge of the die since room is needed for electrical connection buses and the properties of the semiconductor close to the cutting edge are not ideal (FIG. 7). Some space is also needed between the dies for alignment of the pixels. The loss of sensitive width is generally around 100–200 μm.

Therefore there is a need for a method and a device which facilitate the forming of a long rectangular sensor consisting of multiple sensors in line with a minimum loss of data at the borders between the sensors.

SHORT DESCRIPTION OF THE INVENTION

An object of the present invention is to provide a method and a sensor device for a scanning digital radiographic system which offers a multiple sensor arrangement producing continuous data acquisition along the entire length of the sensor device designed according to the invention.

By placing the sensor die border edges at an angle in relation to the scanning direction there is no longer a total loss of data at any position along the longitudinal extension of a long rectangular detector. Instead some loss of data is encountered over a certain range of the scanning width. If the portion of data that is lost is small compared to the total amount of data collected from that position the image can easily be reconstructed by means of the imaging scanning system circuitry or software. The invention as claimed is set forth by the independent claim 1 and in the dependent claims 2–6 a number of different embodiments according to the invention are set forth.

SHORT DESCRIPTION OF THE DRAWINGS

The invention will be described by preferred embodiments to be contemplated with reference to the accompanying drawings wherein like reference numerals are used throughout to designate like parts. In the drawings.

Figure 1:
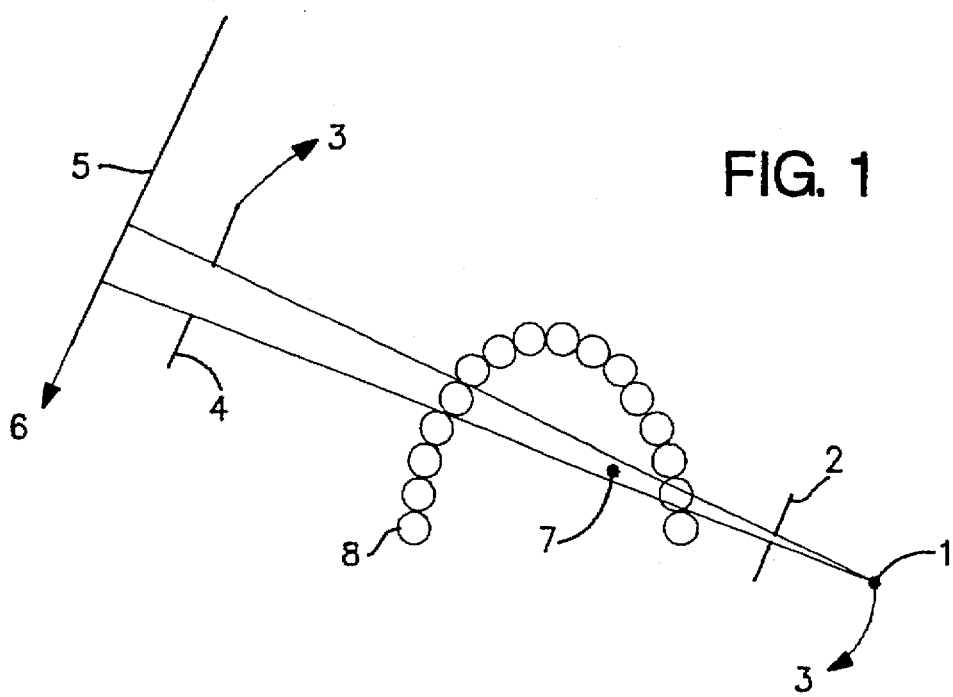
FIG. 1 shows a traditional panoramic narrow slit rotational radiography with film.
Figure 2:
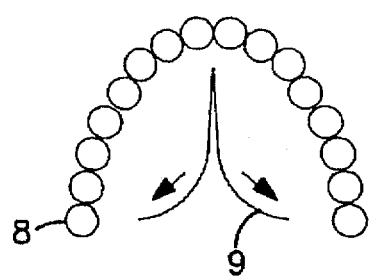
FIG. 2 shows dental arch with a motion path of the rotational axis during an exposure sequence.
Figure 3:
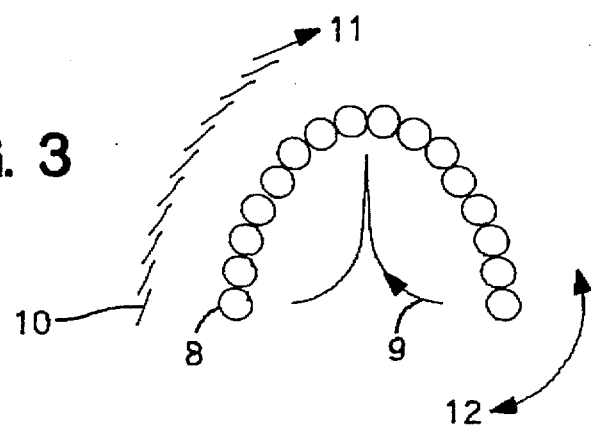
FIG. 3 shows a motion of the detector during a part of an exposure sequence from one position to another and at the same time the x-ray focal spot moves along the path indicated by the arrow and the rotational axis is moved along a path according to FIG. 2.
Figure 4:
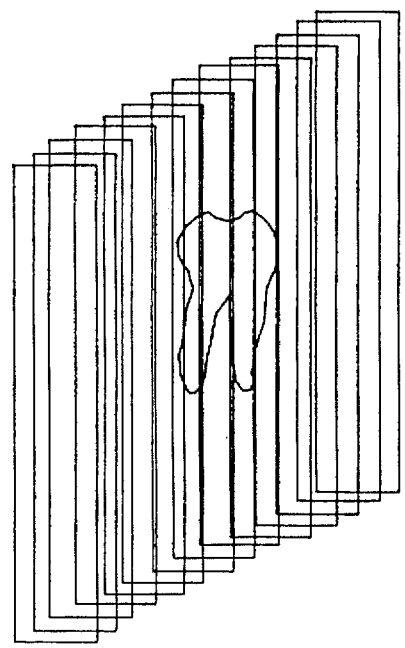
FIG. 4 shows an adding up of vertically oriented, horizontally shifted, narrow x-ray images creating an added up radiogram covering a larger area than a single image.
Figure 5:
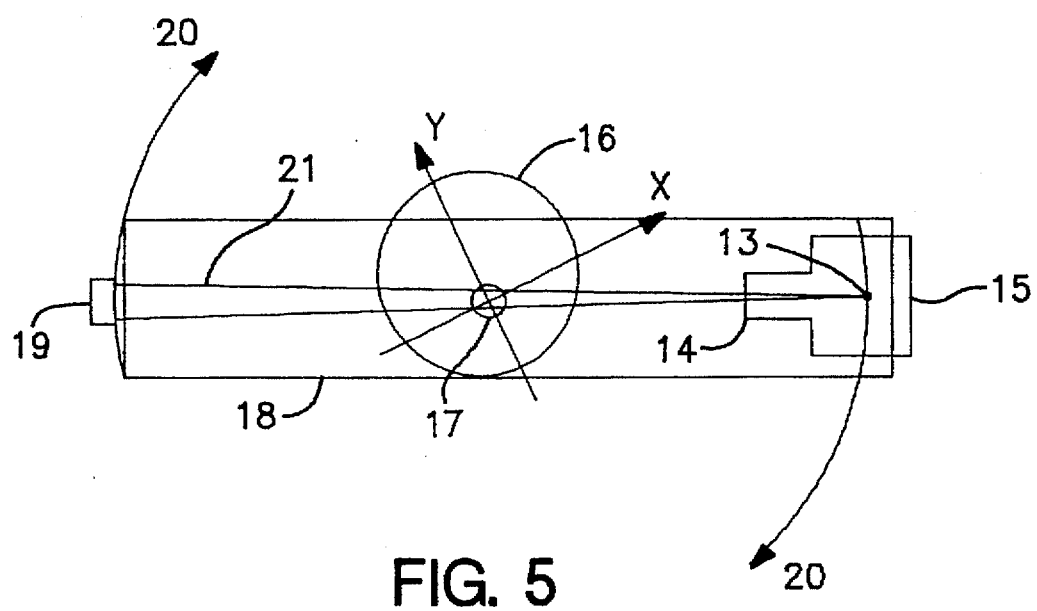
Figure 6:
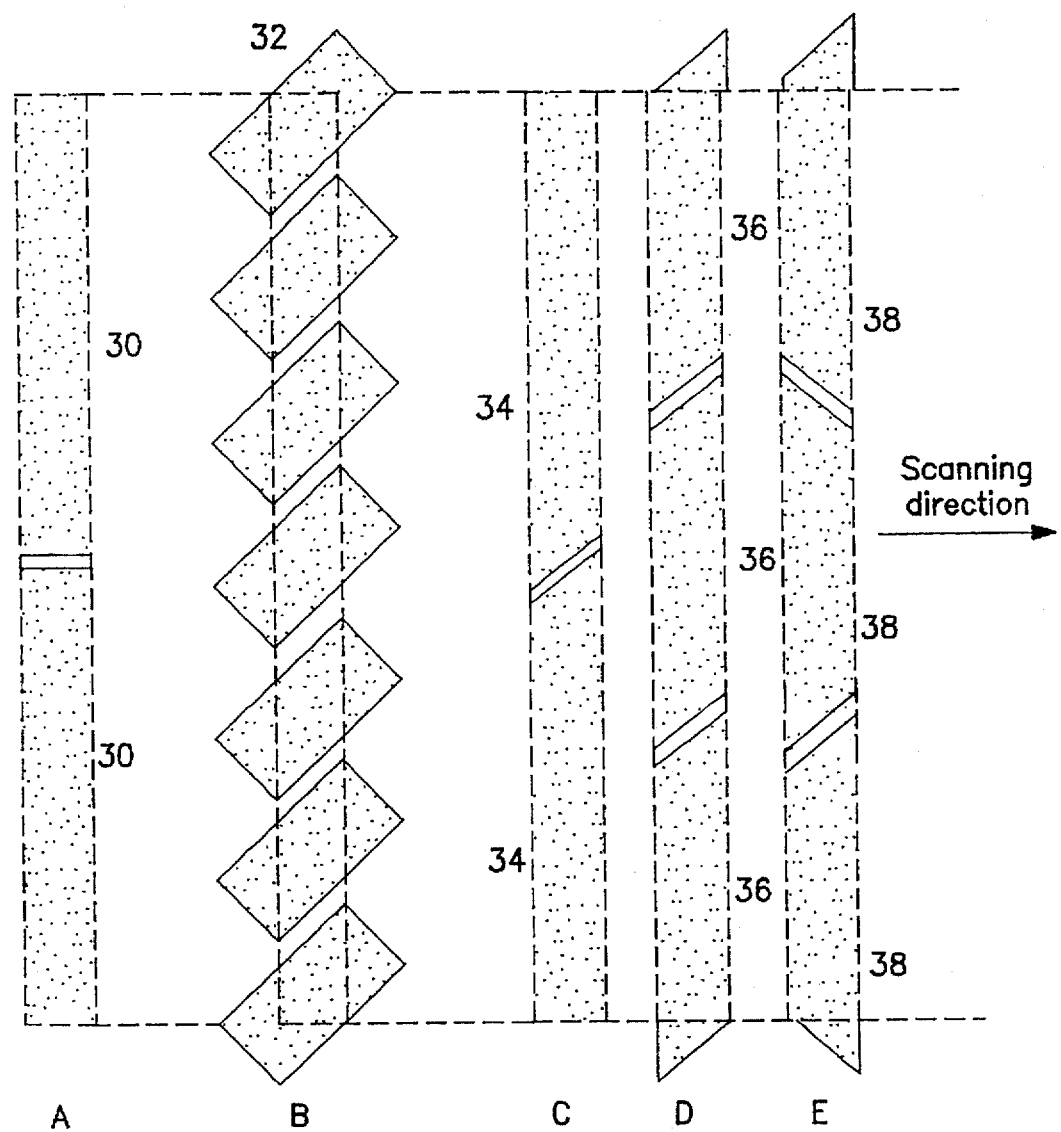
Figure 7:
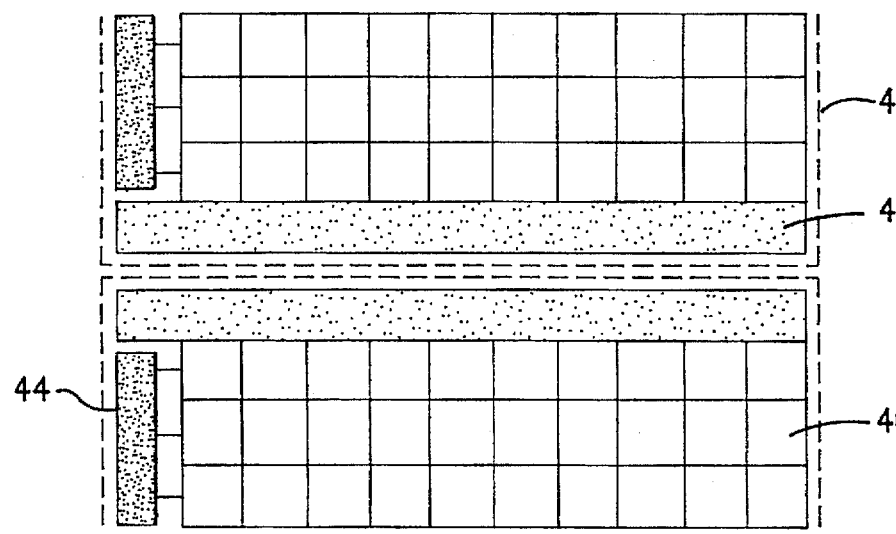
Figure 8:
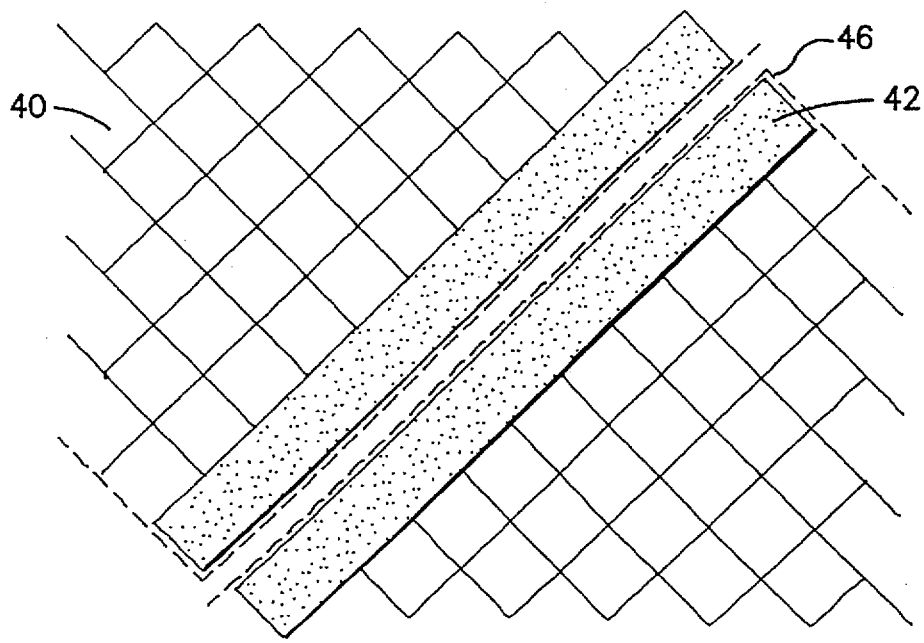
Figure 9:
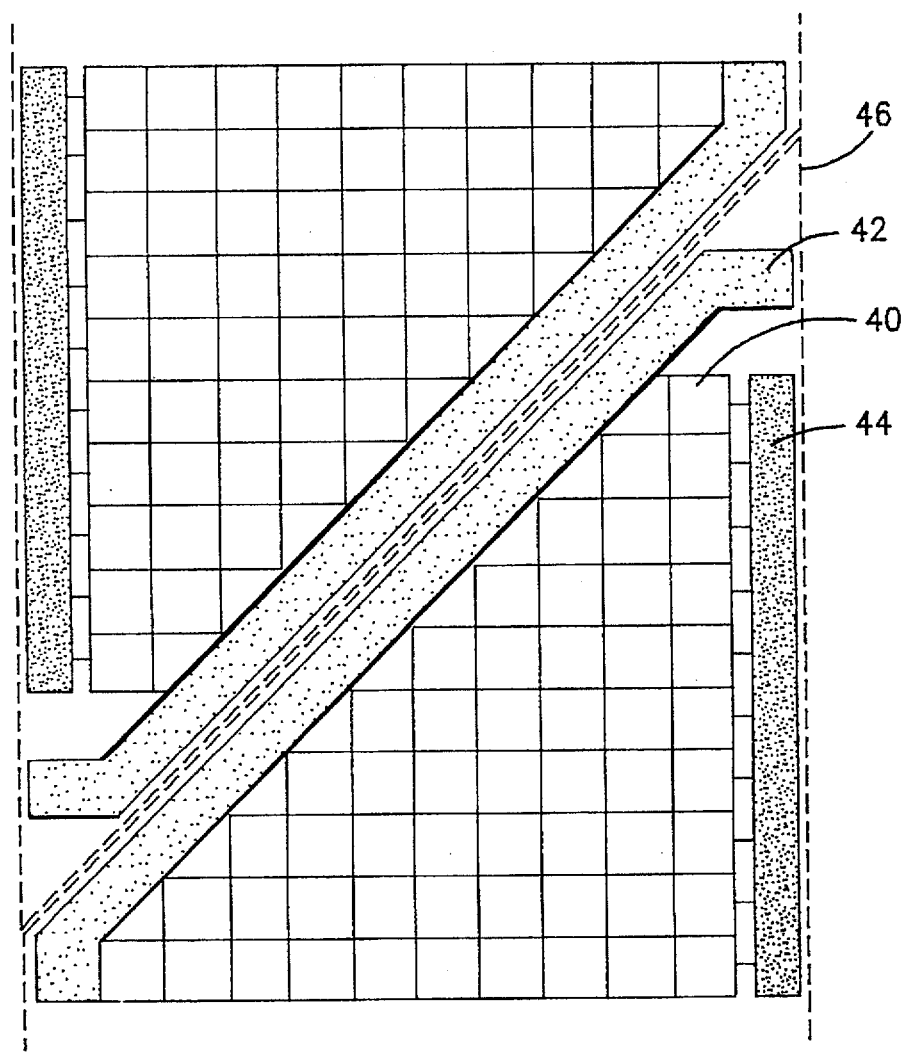

FIG. 5 demonstrates in a plane view a preferred embodiment utilizing a detector comprising a sensor arrangement according to the present invention;

FIG. 6 demonstrates different arrangement for a scanning system with a scanning height larger than the single sensor segment length, the desired imaging window being indicated with a dotted line for each sensor arrangement;

FIG. 7 shows a close up of the sensor segment joint of FIG. 6A demonstrating a detailed picture of the border between the two sensor segments with rectangular shape mounted in line;

FIG. 8 shows a close up of FIG. 6B as a detailed picture of the border between sensor segments using rectangular sensors mounted in an angle to the scanning direction; and FIG. 9 shows details of the border between sensor segments according to the present invention demonstrated in FIGS. 6C–6E having pixels oriented in the scanning direction whereby only a fraction of the data will be lost at the border.

DESCRIPTION OF A PREFERRED EMBODIMENT

An illustrative embodiment of the current invention comprises according to FIG. 5 a case 15 containing an x-ray source 13 and in rigid mechanical connection with a rectangular imaging detector 19 having its long sides vertically oriented. This x-ray source/detector assembly 18 is rotatable around a vertically oriented axis 17 that is movable between any positions within a horizontal plane 16. Close to the x-ray source 13 in the case 15 there is a collimator 14 provided with a slit which together serves to direct the x-ray beam to the detector and to adapt the cross section of beam at the detector to approximately match the active area of the detector 19 comprising a sensor arrangement according to the present invention. The beam area is matched to the detector area to avoid more radiation to the patient than what is required for the acquirement of the images. A second reason for limiting the beam area is to reduce the amount of secondary radiation induced in the object. Excess secondary radiation decreases the image quality.

In FIG. 6 is demonstrated a number of different embodiments to obtain an elongated detector area which is larger than what may be obtained by a single semiconductor die for a scanning dental digital radiographic system according to FIG. 5.

FIG. 6A shows a method according to the state of the art to join two or more sensor elements. In FIG. 7 is demonstrated an enlarged view of the area around the border where the adjacent sensor elements 30 are joined to form the total elongated rectangular detection area wanted. This will by necessity result in a data gap in the image at the joining position of the two elements 30 in the embodiment of FIG. 6A, among other things due to the surface occupied by the metal bus 42 as well as the die cut 46 itself.

A basic arrangement utilizing an idea along with the general method of the present invention is demonstrated in FIG. 6B, utilizing a number of smaller sensor elements 32 formed into an array by tilting the individual sensor element to obtain an overlapping detecting area in the scanning direction. This will however lead to a waste of active area as indicated by the ideal scanning,window inserted in FIG. 6. The orientation of the rows and columns of the sensor pixels 40, as demonstrated in FIG. 8, also complicates the final reconstruction of the image. Anyhow 6B demonstrates a practical cheap way of arranging an elongated sensor by means of a number of easy available small elements 32. Compared to the embodiments according to FIGS. 6C to 6E, there is quite some waste of detector surface, but because of the availability of small rectangular or square elements it will still be economically interesting. By means of the slanting border between the elements there will be no points along the vertical direction lacking data points during the scan. At the borders between individual elements there will be only a small fraction of data missing which easily may be reconstructed by means of hardware or software. The actively operating rectangular surface indicated by the dotted line may easily be defined by a suitable mask.

According to FIGS. 6C to 6E, to save semiconductor surface, the individual sensor elements are not cut using right angles at one or both, generally, of the short ends as in FIGS. 6A or 6B, but instead they are cut with a slanted end side as is demonstrated in the examples of FIGS. 6C, 6D and 6E, then a number of sensors may be mounted in line still with only a fractional loss of data at the border region between the individual adjacent sensor elements. This is illustrated in the embodied applications of FIGS. 6C–6E demonstrating, according to the present invention, individually shaped sensor elements 34, 36, and 38.

FIG. 6C illustrates a case when the entire active detector area is located inside the imaging window and the rows of the sensor pixels 40 are oriented in the scanning direction as may be seen in the enlarged view of FIG. 9. FIG. 6D demonstrates a case using symmetrical sensor sections 36, where the die slanted short end cuts are parallel, while FIG. 6E illustrates a case having the die slanted short end cuts anti-parallel, i.e. at a straight angle i relation to each other for the two short ends of each separate sensor die. However in the embodiments of FIGS. 6D and 6E a little fraction of active area will be wasted at the uppermost, and lowermost portions of the final sensor arrangement as a contribution to the geometry of the die which allows for the same manufacturing process for the short end edges of all the die elements.

The loss of data is controlled by the pixel size, the distance between active areas, the sensor width and the cutting angle. For example a sensor width of 10 mm, a pixel size of 100 µm, a distance between active areas of 200 µm and a cutting angle of 45° gives a loss of data of 4% along the border. An image with such a small loss of data can easily be reconstructed. The minor loss of pixels encountered over the certain range of the scanning width coinciding with the joining of two adjacent sensor dies the image may in this range easily be fully reconstructed by means of the electronic circuitry or the software of the panoramic system.

In the figures and in the example above a cutting angle of 45° has been used. The cutting angle may however vary in a wide range. The optimal angle depends on sensor dimensions, pixel size and distance from last pixel to the edge of the die. The slanted cut sides of the die are provided with a corresponding metal bus 42 or readout section 44 according to standard semiconductor technique well known to a person skilled in the art.

It will be understood by those skilled in the art that various modifications and changes may be made to the present invention without departuring from the spirit and scope thereof, which is defined by the appended claims.

I claim:

1. A method for extending the physical length of a rectangular x-ray detector for a scanning digital radiographic system device comprising a number of individual sensor element dies, characterized by arranging the border line between two adjacent individual sensor elements (34, 36, 38) with a predefined angle in relation to the scanning direction of said radiographic system thereby in the scanning direction creating an overlapping detector sensor element area enabling a continuous data acquisition along the entire length of the multiple sensor element arrangement.

2. The method according to claim 1, characterized by cutting at least one short end of a detector sensor die (34) to a predefined angle in relation to the scanning direction whereby when arranging two such detector dies into an elongated detector arrangement rows and columns of the sensor die pixels (40) are orientated parallel and perpendicular, respectively to the scanning direction, 3. The method according to claim 1, characterized by cutting the short ends of a detector sensor die (36) in parallel to a predefined angle in relation to the scanning direction whereby when arranging two or more such detector dies into an elongated detector arrangement the rows and columns of the sensor die pixels (40) are orientated parallel and perpendicular, respectively to the scanning direction.

4. The method according to claim 1, characterized by cutting the short ends of a detector sensor die (38) anti-parallel to a predefined angle in relation to the scanning direction whereby when arranging two or more such detector dies into an extended detector arrangement the rows and columns of the sensor die pixels (40) are orientated parallel and perpendicular, respectively to the scanning direction.

5. The method according to claim 1, characterized by arranging a number of standard rectangular or square detector elements (32) in an elongated row in which the individual elements are positioned with a slanted angle in respect to the scanning direction.

6. The method according to claim 5, characterized by arranging a mask on top the arrangement of detector elements (32) to define an elongated active sensor area in a direction perpendicular to the scanning direction.

7. An image sensor arrangement utilizing the method of claim 1 characterized in that said sensor arrangement is built up by any convenient combination of individual detector sensor dies (32, 34, 36, 38) forming an elongated rectangular x-ray detector for a scanning digital radiographic system, whereby such a detecter arrangement by means of the overlapping detector sensor element areas in the scanning direction enables a continuous image data acquisition along the entire length of the multiple sensor arrangement with no imaging gaps.

8. An image sensor arrangement utilizing the method of claim 2, characterized in that said sensor arrangement is built up by any convenient combination of individual detector sensor dies (32, 34, 36, 38) forming an elongated rectangular x-ray detector for a scanning digital radiographic system, whereby such a detector arrangement by means of the overlapping detector sensor element areas in the scanning direction enables a continuous image data acquisition along the entire length of the multiple sensor arrangement with no imaging gaps.

9. An image sensor arrangement utilizing the method of claim 3, characterized in that said sensor arrangement is built up by any convenient combination of individual detector sensor dies (32, 34, 36, 38) forming an elongated rectangular x-ray detector for a scanning digital radiographic system, whereby such a detector arrangement by means of the overlapping detector sensor element areas in the scanning direction enables a continuous image data acquisition along the entire length of the multiple sensor arrangement with no imaging gaps.

10. An image sensor arrangement utilizing the method of claim 4, characterized in that said sensor arrangement is built up by any convenient combination of individual detector sensor dies (32, 34, 36, 38) forming an elongated rectangular x-ray detector for a scanning digital radiographic system, whereby such a detector arrangement by means of the overlapping detector sensor element areas in the scanning direction enables a continuous image data acquisition along the entire length of the multiple sensor arrangement with no imaging gaps.

11. An image sensor arrangement utilizing the method of claim 5, characterized in that said sensor arrangement is built up by any convenient combination of individual detector sensor dies (32, 34, 36, 38) forming an elongated rectangular x-ray detector for a scanning digital radiographic system, whereby such a detector arrangement by means of the overlapping detector sensor element areas in the scanning direction enables a continuous image data acquisition along the entire length of the multiple sensor arrangement with no imaging gaps.

12. An image sensor arrangement utilizing the method of claim 6, characterized in that said sensor arrangement is built up by any convenient combination of individual detector sensor dies (32, 34, 36, 38) forming an elongated rectangular x-ray detector for a scanning digital radiographic system, whereby such a detector arrangement by means of the overlapping detector sensor element areas in the scanning direction enables a continuous image data acquisition along the entire length of the multiple sensor arrangement with no imaging gaps.

* * * * *